United States Patent [19]

Wang

[11] Patent Number: 4,889,907

[45] Date of Patent: Dec. 26, 1989

[54] POLYMERIC POLYHYROXY POLYETHER CONTAINING 1,6-DIAZASPIRO-[4.4]NONANE-2,7-DIONE UNITS

[75] Inventor: Pen C. Wang, Houston, Tex.

[73] Assignee: Shell Oil Company, Houston, Tex.

[21] Appl. No.: 245,619

[22] Filed: Sep. 16, 1988

Related U.S. Application Data

[63] Continuation-in-part of Ser. No. 185,574, Apr. 25, 1988, abandoned, which is a continuation-in-part of Ser. No. 172,054, Mar. 23, 1988, and a continuation-in-part of Ser. No. 171,998, Mar. 23, 1988, abandoned.

[51] Int. Cl.$^4$ .................. C08G 59/29; C08G 69/14
[52] U.S. Cl. ........................ 528/96; 528/89; 528/97; 528/117; 528/323

[58] Field of Search ............... 528/96, 97, 117, 323, 528/89

[56] References Cited

U.S. PATENT DOCUMENTS 4,672,102  6/1987  Silvis et al. ................. 528/97

*Primary Examiner*—Harold D. Anderson

[57] ABSTRACT

Novel polymeric polyhydroxy polyethers containing moieties of 2,2-di(oxyphenyl)propane and a 1,6-diazaspiro[4.4] spirodilactam having oxyaryl substituents on each spiro ring nitrogen atom, which moieties are connected by 2-hydroxy-1,3-propylidene connecting groups, are characterized by relatively high glass transition temperatures.

29 Claims, No Drawings

POLYMERIC POLYHYROXY POLYETHER CONTAINING 1,6-DIAZASPIRO-[4.4]NONANE-2,7-DIONE UNITS

This application is a continuation-in-part of copending U.S. patent application Ser. No. 185,574, filed Apr. 25, 1988, now abandoned which is a continuation-in-part of U.S. patent application Ser. No. 172,054, filed Mar. 23, 1988 and Ser. No. 171,998 filed Mar. 23, 1988 now abandoned.

FIELD OF THE INVENTION

This invention relates to a novel class of polymeric polyhydroxy polyethers incorporating within the polymer chain two types of cyclic structure. More particularly, the invention relates to polymeric polyhydroxy polyethers incorporating moieties of a diphenylpropane and a [4.4] spirodilactam having spiro ring nitrogen atoms in the 1- and 6- ring positions.

BACKGROUND OF THE INVENTION

The term "phenoxy resin" is a generic term used to describe the amorphous, high molecular weight poly(hydroxyethers) derived from reaction of diphenols and epichlorohydrin or from the reaction of diphenols and the diglycidyl ether of 2,2-di(4-hydroxyphenyl)propane. The resins are tough, high modulus thermoplastic materials of established commercial utility. For example, a commercial resin marketed by Union Carbide as UCAR Resin is produced from epichlorohydrin and 2,2-di(4-hydroxyphenyl)propane. The product of the reaction of 2,2-di(4-hydroxyphenyl)propane and its corresponding diglycidyl ether is a second example of a commercial phenoxy resin. Such resins have utility in applications such as molded articles, films and packaging materials, coatings and adhesives but have not been extensively used as engineering thermoplastics because of relatively low glass transition temperatures.

The reaction product of epichlorohydrin and a spirobiindol is disclosed in U.S. Pat. No. 4,672,102 wherein the product is said to have high heat distortion temperatures and the values reported are from about 131° C. to about 153° C. depending upon the nature of the substituents present. The corresponding value for the reaction product of epichlorohydrin and 2,2-di(4-hydroxyphenyl)propane was 88° C. It would be of advantage to provide a class of novel polycyclic phenoxy-type resins having comparable or even higher glass transition temperatures.

DESCRIPTION OF THE INVENTION

The novel polymeric polyhydroxy polyethers of the invention are characterized by the presence of divalent 2-hydroxy-1,3-propylene connecting groups, i.e., by —CH$_2$—CH(OH)—CH$_2$— groups, which serve to connect alternating 2,2-di(oxyphenyl)propane moieties and moieties of a 1,6-diazaspiro[4.4]nonane-2,7-dione having oxyaryl-containing substituents on each of the spiro ring nitrogen atoms of the spirodilactam. Polyhydroxy polyethers of a wide variety of structural types are suitable as the phenoxy resins of the invention. However, a preferred class of polyhydroxy polyethers is represented by the repeating formula

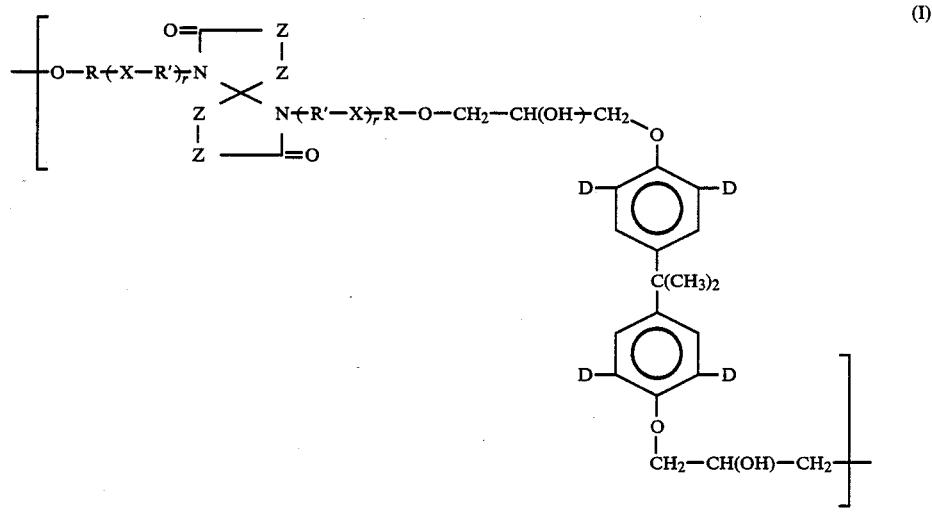

(I)

wherein Z independently is >C(Z')$_2$ in which Z' independently is hydrogen, lower alkyl of up to 4 carbon atoms inclusive, preferably methyl or halogen, preferably lower halogen fluorine or chlorine, or Z is such that two adjacent Z moieties form a ring system Z" of from 5 to 7 ring atoms, up to two of which are heteroatoms selected from nitrogen, oxygen or sulfur with the remainder of the ring atoms being carbon atoms, there being up to 15 carbon atoms inclusive in each Z", two of which form a connecting bridge between a carbonyl carbon atom, i.e., a carbon atom in one of the 2- or 7-spiro ring positions, and the central or spiro carbon atom, i.e., the carbon atom common to the two spiro rings. R in the above formula I independently is aromatic of up to 15 carbon atoms and up to two aromatic rings, inclusive, and R' independently is R or aliphatic of up to 10 carbon atoms inclusive. Each of R and R' independently is hydrocarbyl, i.e., contains only atoms of carbon and hydrogen, or is substituted hydrocarbyl containing additional atoms such as halogen, preferably the middle halogens chlorine and bromine, in the form of inert substituents. The term r in the above formula I independently is 0 or 1 and X independently is a direct valence bond, alkylene of up to 8 carbon atoms inclusive, oxo, thio, sulfonyl, carbonyl, dioxyphenylene, i.e., 2,2-di(oxyphenyl)propane, i.e.,

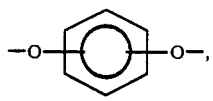

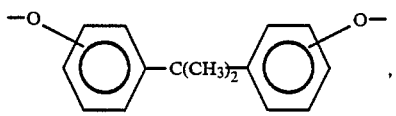

or dioxydiphenylene, i.e.,

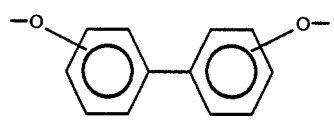

and D independently is hydrogen, lower alkyl or middle halogen. The polymeric polyhydroxy polyeters of formula I will be defined further in terms of the monomers used in their production, largely for reasons of clarity and simplicity. However, the preferred polyethers of formula I are those wherein each r is 0, R is phenyl and D is hydrogen. Particularly preferred are such polyethers wherein the linkage connecting each R substituent of the spirodilactam moiety to the adjacent hydroxypropylene moiety is para across the phenylene ring to the linkage connecting the R substituent to the spiro ring nitrogen, i.e., R is p-phenylene.

The polymeric polyethers are produced by reaction of a 1,6-diazaspiro[4.4]nonane-2,7-dione having a hydroxyaryl-containing substituent on each spiro ring nitrogen atom, or alternativly the diglycidyl ether thereof, with a 2,2-di(4-dihydroxyphenyl)propane or alternatively the diglycidyl ether thereof, with the proviso that one reactant is a dihydroxy reactant and the other reactant is a diglycidyl ether reactant. By way of further illustration, the polyethers of the invention are produced (1) by reaction of 1,6-diazaspiro[4.4]nonane-2,7-dione having a hydroxyaryl-containing substituent on each spiro ring nitrogen atom and a 2,2-di(4-glycidyloxyphenyl)propane or (2) by reaction of a 1,6-diazaspiro[4.4]nonane-2,7-dione having a glycidyloxyaryl substitutent on each spiro ring nitrogen atom with a 2,2-di(4-hydroxyphenyl)propane.

In terms of the preferred polymeric polyhydroxy polyethers of the above formula I, the spirodilactam reactant is represented by the formula

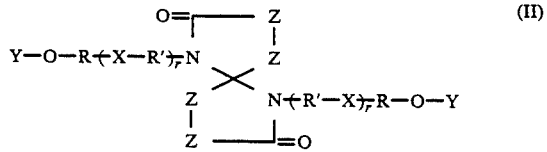

wherein R, R', r, X and Z have the previously stated significance and Y is hydrogen or glycidyl, and the diphenylpropane reactant is represented by the formula

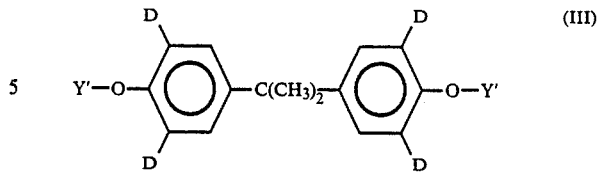

wherein D has the previously stated meaning and Y' is hydrogen or glycidyl, with the proviso that Y and Y' are not the same.

Spirodilactam reactants of the above formula II where Y is hydrogen, and methods for the production of the spirodilactams, are disclosed and claimed in copending U.S. patent applications Ser. No. 172,000, filed Mar. 23, 1988, serial No. 172,052, filed Mar. 23, 1988, and Ser. No. 245618, filed Sept. 16, 1988, each of which is incorporated herein by reference. The spirodilactam reactants of the above formula II wherein Y is glycidyl are described and claimed in copending U.S. Pat. application Ser. No. 172,054, filed Mar. 23, 1988 and Ser. No. 245,434, filed Sept. 16, 1988, each of which is incorporated herein by reference, where methods for the production of these spirodilactam reactants are also found.

The diphenylpropane reactants of formula III wherein Y' is hydrogen or glycidyl are known compounds or are produced from known compounds by known methods.

Illustrative of the spirodilactam reactant of formula II are 1,6-di(4-hydroxyphenyl)-1,6-diazaspiro[4.4]nonane-2,7-dione; 1,6-di(4-glycidyloxyphenyl)-1,6-diazaspiro[4.4]nonane-2,7-dione; 1,6-di(4-hydroxyphenyl)-3,8-dimethyl-1,6-diazaspiro[4.4]nonane-2,7-dione; 1,6-di(3-glycidyloxyphenyl)-3,4,8,9-dibenzo-1,6-diazaspiro[4.4]nonane-2,7-dione; 1,6-di(3-hydroxy-4-chlorophenyl)-3,4-dimethyl-1,6-diazaspiro[4.4]nonane-2,7-dione; 1,6-di[4-(4-glycidyloxyphenyloxy)phenyl]-1,6-diazaspiro[4.4]nonane-2,7-dione; 1,6-di[4-(3-hydroxybenzoyl)phenyl]1,6-diazaspiro[4.4]nonane-2,7-dione; 1,6-di[4-(4'-glycidyloxybiphenyl)]-3,3-dimethyl-1,6-diazaspiro[4.4]nonane-2,7-dione; 1,6-di[1-(4-hydroxynaphthyl)]-1,6-diazaspiro[4.4]nonane-2,7-dione; 1,6-di(4-glycidyloxyphenyl)-3,4,8,9-cyclohexano-1,6-diazaspiro[4.4]nonane-2,7-dione, 1,6-di[4-(4-hydroxyphenylisopropyl)phenyl]-1,6-diazaspiro[4.4]nonane-2,7-dione.

Illustrative of the diphenylpropane reactants of formula III are 2,2-di(4-hydroxyphenyl)propane; 2,2-di(4-glycidyloxyphenyl)propane; 2,2-di(4-hydroxy-3-methylphenyl)propane; 2,2-di(4-glycidyloxy-3,5-dimethylphenyl)propane; 2,2-di(4-hydroxy-3,5-dibromophenyl)propane; 2,2-di(4-hydroxy-3-chlorophenyl)propane and 2-(4-hydroxy-3,5-dibromophenyl)-2-(4-hydroxyphenyl)propane.

The diphenylpropane reactants and the spirodilactam reactant will combine in an equimolar relationship to give the same product regardless of which reactant is the hydroxy reactant and which is the glycidyloxy reactant. In practice, providing to a reaction mixture a ratio of one reactant to the other reactant of from about 4:1 to about 1:4 is suitable although reactant ratios which are substantially stoichiometric, e.g., from about 1.25:1 to about 1:1.25 are preferred. Reaction is conducted by contacting the spirodilactam reactant and the diphenylpropane reactants and maintaining the resulting mixture under polymerization conditions. It is useful in most embodiments of the process of the invention to employ a polymerization catalyst which is preferably a quaternary phosphonium or ammonium salt, particularly a quaternary phosphonium or ammonium halide although salts such as a phosphonium acetate or bicarbonate are also useful. Such catalysts are conventional in this type of process and are often alkyltriphenylphosphonium salts. Ethytriphenylphosphonium bromide or ethyltriphenylphosphonium iodide are preferred. The catalyst is not required but when present the phosphonium salt is present in catalytic quantities. Amounts of phosphonium salt up to about 5% by weight, based on total reactants, are satisfactory.

Suitable reaction temperatures for the reaction of the spirodilactam reactant and the diphenylpropane reactant and the diphenylpropane reactant are above about 150° C. and preferably above about 180° C., but are generally below about 300° C. Reaction pressures of about atmospheric are suitable although higher or lower pressures may also be used if sufficient to maintain the reaction mixture in a liquid phase at reaction temperature. Reactant contact during reaction is maintained by conventional methods such as shaking or stirring. The polymeric polyether product is typically obtained as a solid upon cooling of the product mixture subsequent to reaction. The product is often used as such without the need for further purification but the product is purified if desired by conventional methods such as by dissolving the product mixture in a suitable solvent e.g., an ether such as tetrahydrofuran, and re-precipitating the product with an alkanol such as methanol.

The molecular weight of the product will be influenced by the reaction conditions employed, particularly the reaction temperature. Polymeric polyhydroxy polyethers of molecular weight of from about 10,000 to about 100,000 are preferred in part because of the desirable properties they exhibit. The products are characterized by relatively high glass transition temperatures, typically above 155° C. or even higher. The polyethers find utility in the applications conventionally associated with phenoxy resins but are additionally useful in engineering applications such as molded containers for food and drink which are frequently exposed to elevated temperatures. The polymeric polyethers are processed by means of the usual techniques such as injection, compression or blow molding to produce films and shaped articles.

The invention is further illustrated by the following Illustrative Embodiments and Comparative Example (not of the invention) which should not be construed as limiting.

ILLUSTRATIVE EMBODIMENT I

A mixture of 3.4 g (0.01 mols) of 2,2-di(4-glycidyloxyphenyl)propane, 3.38 g (0.01 mole) of 1,6-di(4-hydroxyphenyl)-1,6-dazaspiro[4.4]-nonane-2,7-dione and 0.1855 g (0.0005 mole) of ethytriphenylphosphonium bromide was placed in a reactor of 50 ml capacity equipped with a mechanical stirrer and a condenser. The reaction mixture was stirred while being warmed to 200° C. and maintained at 200° C. for 6 hours. The resulting mixture was then cooled and the reaction product was isolated as a hard resin with a glass transition temperature of 157° C.

ILLUSTRATIVE EMBODIMENT II

A mixture of 1.14 g (0.005 mole) of 2,2-di(4-hydroxyphenyl)propane, 2.25 g (0.005 mole) of 1,6-di(4-glycidyloxyphenyl)-1,6-diazaspiro[4.4]nonane-2,7-dione and 0.1855 g (0.0005 mole) of ethytriphenylphosphonium bromide was placed in a reactor of 50 ml capacity equipped with a mechanical stirrer and a condenser. While being stirred, the reaction mixture was warmed to 200° C. and maintained at 200° C. for 6 hours. The resulting mixture was cooled and the reaction product isolated as a hard resin with a glass transition temperature of 156° C.

COMPARATIVE EXAMPLE

The reaction product of 2,2-di(4-glycidryloxyphenyl)propane and 2,2-di(4-hydroxyphenyl)propane was produced by the procedure of Illustrative Embodiment I. The product, a commercial resin, had a glass transition temperature of 87° C.

What is claimed is:

1. A polymeric, polyhydroxy polyether which comprises alternating units of a 2,2-di(oxyphenyl)propane moiety and a 1,6-diazaspiro[4.4]nonane-2,7-dione moiety having oxyaryl-containing substituents on each spiro ring nitrogen atom, said alternating units being connected by 2-hydroxy-1,3-propylene connecting groups.

2. The polymeric, polyhydroxy polyether of claim 1 represented by the repeating formula

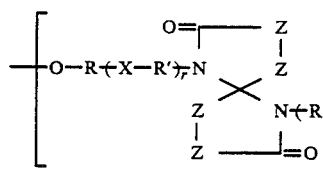
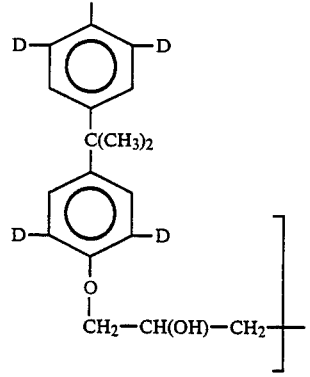

wherein Z independently is $>C(Z')_2$ in which $Z'$ independently is hydrogen, lower alkyl, fluorine or chlorine, or Z is such that two adjacent Z moieties form a ring system $Z''$ of from 5 to 7 ring atoms, up to two of which are heteroatoms selected from nitrogen, oxygen or sulfur with the remainder of the ring atoms being carbon atoms, there being up to 15 carbon atoms in each $Z''$, two of which form a connecting bridge between a carbonyl carbon atom and the central spiro carbon atom, R independently is aromatic of up to 15 carbon atoms an up to 2 aromatic rings, inclusive, $R'$ independently is R or aliphatic of up to 10 carbon atoms inclusive, r independently is 0 or 1, X independently is a direct valence bond or X independently is alkylene of up to 8 carbon atoms inclusive, oxo, thio, sulfonyl, carbonyl, dioxyphenylene, 2,2-di(oxyphenyl)propane or dioxydiphenylene, and D independently is hydrogen, lower alkyl, chlorine or bromine.

3. The polyether of claim 2 wherein each D is bromo.

4. The polyether of claim 2 wherein each D is hydrogen.

5. The polyether of claim 4 wherein each r is 0.

6. The polyether of claim 5 wherein each Z is $C(Z')_2$.

7. The polyether of claim 6 wherein $Z'$ independently is hydrogen or methyl.

8. The polyether of claim 7 wherein each $Z'$ is hydrogen.

9. The polyether of claim 7 wherein R is p-phenylene.

10. The polyether of claim 8 wherein R is

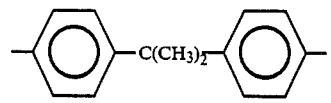

11. The polyether of claim 9 wherein each $Z''$ is pyridino.

12. A process for producing a polymeric, polyhydroxy polyether by contacting (1) a spirodilactam reactant of the formula

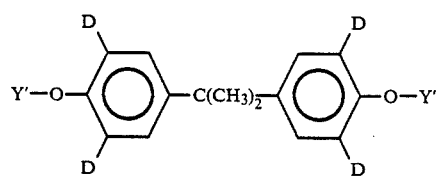

wherein Z independently is $>C(Z')_2$ in which $Z'$ independently is hydrogen or lower alkyl or Z is such that two adjacent Z moieties form a ring system $Z''$ of from 5 to 7 ring atoms, up to two of which are heteroatoms selected from nitrogen, oxygen or sulfur with the remainder of the ring atoms being carbon atoms, there being up to 15 carbon atoms inclusive in each $Z''$, two of which form a connecting bridge between a carbonyl carbon atom and the spiro carbon atom, R independently is aromatic of up to 15 carbon atoms and up to two aromatic rings, inclusive, $R'$ independently is R or aliphatic of up to 10 carbon atoms inclusive, r independently is 0 or 1, X independently is a direct valence bond or X independently is alkylene of up to 8 carbon atoms inclusive, oxo, thio, sulfonyl, carbonyl, dioxyphenylene, 2,2-di(oxyphenyl)propane or dioxydiphenylene, and Y is hydrogen or glycidyl, and (2) a diphenylpropane reactant of the formula $$Y'-O-\underset{D}{\underset{D}{\bigcirc}}-C(CH_3)_2-\underset{D}{\underset{D}{\bigcirc}}-O-Y'$$

wherein D independently is hydrogen, lower alkyl or middle halogen and $Y'$ is hydrogen or glycidyl with the proviso that Y and $Y'$ are not the same, under polymerization conditions in the presence of up to 5% by weight of a quaternary phosphonium salt catalyst.

13. The process of claim 12 wherein each D is bromo.

14. The process of claim 12 wherein each D is hydrogen and $Y'$ is glycidyl.

15. The process of claim 14 wherein each Z is acyclic.

16. The process of claim 15 wherein R is 0 and R is phenylene.

17. The process of claim 16 wherein the spirodilactam reactant is 1,6-di(hydroxyphenyl)-1,6-diazaspiro[4.4]nonane-2,7-dione.

18. The process of claim 17 wherein the hdroxyphenyl moiety is 4-hydroxyphenyl.

19. The process of claim 15 wherein the spirodilactam reactant is 1,6-di[4-(4-hydroxyphenylisopropyl)phenyl]-1,6-diazaspiro[4.4]nonane-2,7-dione.

20. The process of claim 14 wherein adjacent Z moieties taken together form Z''.

21. The process of claim 20 wherein each r is 0 and R is phenylene.

22. The process of claim 21 wherein the spirodilactam reactant is 1,6-di(4-hydroxyphenyl)-3,4,8,9-dibenzo-1,6-diazaspiro[4.4]nonane-2,7-dione.

23. The process of claim 12 wherein D is hydrogen and Y' is hydrogen.

24. The process of claim 23 wherein each Z is acyclic.

25. The process of claim 23 wherein each r is 0 and R is phenylene.

26. The process of claim 25 wherein the spirodilactam reactant is 1,6-(4-glycidyloxyphenyl)-1,6-diazaspiro[4.4]nonane-2,7-dione.

27. The process of claim 23 wherein adjacent Z moieties taken together form Z''.

28. The process of claim 27 wherein each r is 0.

29. The process of claim 28 wherein the spirodilactam is 1,6-di(4-glycidyloxyphenyl)-3,4,8,9-dibenzo-1,6-diazaspiro[4.4]nonane-2,7-dione.

* * * * *